(12) United States Patent
Schmitzer et al.

(10) Patent No.: US 10,435,525 B2
(45) Date of Patent: Oct. 8, 2019

(54) FILM WITH ADJUSTABLE WATER VAPOR-PERMEABILITY

(71) Applicant: INFIANA GERMANY GMBH & CO. KG, Forchheim (DE)

(72) Inventors: Siegfried Schmitzer, Kürnach (DE); Michael Schuhmann, Großhabersdorf (DE)

(73) Assignee: INFIANA GERMANY GMBH & CO. KG, Forchheim (DE)

( * ) Notice: Subject to any disclaimer, the term of this patent is extended or adjusted under 35 U.S.C. 154(b) by 374 days.

(21) Appl. No.: 15/079,530

(22) Filed: Mar. 24, 2016

(65) Prior Publication Data

US 2016/0229966 A1  Aug. 11, 2016

Related U.S. Application Data

(63) Continuation of application No. PCT/EP2014/002695, filed on Oct. 2, 2014.

(30) Foreign Application Priority Data

Oct. 8, 2013  (DE) ........................ 10 2013 016 583

(51) Int. Cl.
| | |
|---|---|
| *C08J 5/18* | (2006.01) |
| *C09J 7/25* | (2018.01) |
| *C09J 7/29* | (2018.01) |
| *B32B 27/30* | (2006.01) |

(Continued)

(52) U.S. Cl.
CPC .............. *C08J 5/18* (2013.01); *A61L 15/225* (2013.01); *B32B 27/30* (2013.01); *B32B 27/34* (2013.01); *C09J 7/25* (2018.01); *C09J 7/29* (2018.01); *B32B 2307/7246* (2013.01); *C08J 2377/06* (2013.01); *C08J 2431/04* (2013.01); *C09J 2421/00* (2013.01); *C09J 2433/00* (2013.01); *C09J 2453/006* (2013.01); *C09J 2475/00* (2013.01); *C09J 2483/00* (2013.01)

(58) Field of Classification Search
None
See application file for complete search history.

(56) References Cited

U.S. PATENT DOCUMENTS

| | | | |
|---|---|---|---|
| 5,614,588 | A | 3/1997 | Steenblock et al. |
| 5,703,161 | A | 12/1997 | Steenblock et al. |
| 5,800,928 | A | 9/1998 | Fischer et al. |

(Continued)

FOREIGN PATENT DOCUMENTS

| | | |
|---|---|---|
| DE | 44 10 921 A1 | 10/1995 |
| DE | 100 18 937 A1 | 10/2001 |

(Continued)

OTHER PUBLICATIONS

German Search Report dated Jan. 4, 2014.

(Continued)

*Primary Examiner* — Frank D Ducheneaux

(74) *Attorney, Agent, or Firm* — The Dobrusin Law Firm, P.C.

(57) ABSTRACT

Hydrophobic breathable film based on a polymer mixture of A) at least one hydrophilic elastomer block copolymer made of at least one polyamide block and at least one polyalkylene oxide block and B) at least one thermoplastic polymer, which regulates the steam-permeability of the breathable film.

18 Claims, 2 Drawing Sheets

(51) Int. Cl.
*B32B 27/34* (2006.01)
*A61L 15/22* (2006.01)

(56) References Cited

U.S. PATENT DOCUMENTS

| | | | |
|---|---|---|---|
| 5,840,807 A | 11/1998 | Frey et al. | |
| 5,888,597 A | 3/1999 | Frey et al. | |
| 8,309,211 B2 * | 11/2012 | Mehta | E04D 12/002 428/220 |

FOREIGN PATENT DOCUMENTS

| | | |
|---|---|---|
| DE | 69 63 1449 T2 | 9/2004 |
| EP | 0 476 963 A2 | 3/1992 |
| EP | 0 657 502 A1 | 6/1995 |
| WO | 2005/030860 A1 | 4/2005 |
| WO | 2012/141735 A1 | 10/2012 |

OTHER PUBLICATIONS

International Search Report dated Nov. 27, 2014, dated Dec. 4, 2014.
English Translation of International Search Report dated Nov. 27, 2014, dated Dec. 4, 2014.
Kunststoff-Handbuch vol. VI, Polyamide Verlag Munich, 1966 [Polyamides], Carl Hanser Verlag Munich, 1966.
Melvin I. Kohan, Nylon Plastics Handbook, Carl Hanser Verlag, Munich, 1995.

* cited by examiner

FILM WITH ADJUSTABLE WATER VAPOR-PERMEABILITY

This application is a Continuation of International Patent Application No. PCT/EP2014/002695, filed on Oct. 2, 2014, which claims foreign priority benefits under 35 U.S.C. § 119 of German Patent Application No. 10 2013 016 583.0, filed Oct. 8, 2013, the disclosure of which patent application is incorporated herein by reference.

The present invention relates to a single-layer or multilayer, breathable film which repels aqueous liquids, preferably water, the water vapor transmission rate of which is from 20 to ≥3000 g/m²·24 h (at 23° C., 100% relative humidity and film thickness: 75 μm) measured in accordance with ASTM F1249, comprising at least one layer based on a polymer mixture of
A) at least one hydrophilic, elastomeric block copolymer built of at least one polyamide block and of at least one polyalkylene oxide block with water vapor transmission rate of at least 1200 g/m²·24 h (at 23° C., 100% relative humidity and film thickness: 75 μm), measured in accordance with ASTM F1249, and
B) for regulating the water vapor transmission rate of the breathable film, at least one thermoplastic polymer with water absorption of 2% by weight,
and also to the use of these films as large-surface-area sheeting material, preferably as roof-lining membrane, or a component of roof linings, for the production of adhesive tapes, preferably of adhesive tapes used in the construction sector, as part, preferably substrate layer, of plasters of any type, or as part, preferably as liquid-impermeable protective film, of hygiene products or of incontinence products.

BACKGROUND OF THE INVENTION

Water-repellent, breathable films have a wide field of application. Depending on the water vapor permeability these films are used in the hygiene sector for diapers or incontinence products or in the construction sector as part of a building sheeting or for the production of adhesive tapes which by way of example are used for the adhesive bonding of films or sheets for preparing a building sheeting.

In the hygiene sector liquid-repellent and/or liquid-impermeable, breathable films are arranged preferably as protective films, in particular underwear-protecting films arranged as external surface, facing away from the body, of a hygiene product or incontinence product, because essential properties are not only impermeability to aqueous liquids but also dissipation of the water vapor that is emitted from the skin region covered by the respective product, for example through sweating. Accordingly these protective films of hygiene products or of incontinence products must, although they are impermeable to aqueous liquids, in particular water, have an adequate water vapor transmission rate, i.e. must be breathable.

In the construction sector, in particular in the external region of a house, e.g. on roofs or on facades, films are often installed in the form of large-surface-area sheet material as "wind proofing" or "rain proofing" material. The arrangement of these protective covering materials is mostly above the insulation layer and below the actual external covering or external layer composed by way of example of tiles, fiber-reinforced concrete panels, or the like. These protective covering sheets are usually laid so as to overlap, and at least the resultant joints are adhesive-bonded with single-sided adhesive tapes.

This avoids air flows or moisture penetration through any open joints in the region of the insulation layer, even if wind, snow, or rain penetrates through the external layer. These air flows comprising cold and/or moist external air reduce the effect of insulation, and this should as far as possible be avoided.

On the other hand, these protective coverings, i.e. large-surface-area sheeting material, and also the adhesive tapes, must at the same time be permeable to water vapor, in order to ensure outward transport of moisture from the interior of the house, and thus avoid the risk of rot and mold formation.

The breathable films used for this purpose, known from the prior art, and products produced therefrom, exhibit disadvantages in their handling.

By way of example, adhesive tapes, in particular with appropriately oriented water vapor transmission rate and with substrate layers made of known breathable, multilayer films, can have a tendency toward delamination, and this can lead to permeability, e.g. in the case of roof linings.

It was therefore an object of the present invention to provide a breathable film that repels aqueous liquids, preferably water, and that ensures excellent handling and long-lasting quality, and the water vapor transmission rate of which can be adjusted in accordance with the requirements of the respective intended purpose.

SUMMARY OF THE INVENTION

According to the invention this object is achieved via provision of a single-layer or multilayer, breathable film which repels aqueous liquids, the water vapor transmission rate of which is from 20 to ≥3000 g/m²·24 h (at 23° C., 100% relative humidity and film thickness: 75 μm) measured in accordance with ASTM F1249, comprising at least one layer based on a polymer mixture of
A) at least one hydrophilic, elastomeric block copolymer built of at least one polyamide block and of at least one polyalkylene oxide block having a water vapor transmission rate of at least 1200 g/m²·24 h, determined as mentioned before, and
B) for regulating the water vapor transmission rate of the breathable film, at least one thermoplastic polymer with water absorption ≤2% by weight, and optionally conventional auxiliaries.

DETAILED DESCRIPTION

Figure 1:
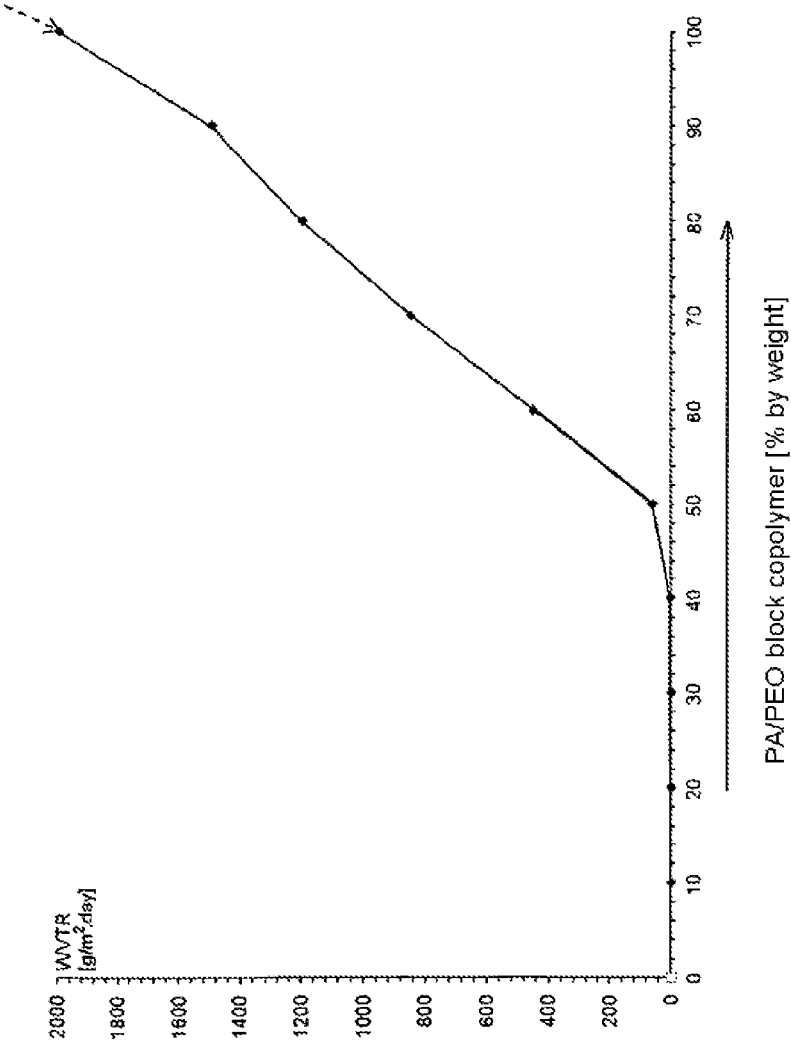
FIG. 1 is a graph showing the dependency of the water vapor transmission rate of a mixture of LDPE and a block copolymer made of PA6 blocks and of polyethylene oxide blocks.

Block copolymers made of polyamide blocks and of polyalkylene oxide blocks are known.

However, it has surprisingly been found that of the known block copolymers made of polyamide blocks and of polyalkylene oxide blocks only the corresponding hydrophilic block copolymers are suitable for the production of the inventive breathable films and use of these.

The hydrophilicity of the block copolymers used according to the invention is determined by the method described thereafter, in that the water absorbency of a film made of the respective block copolymer is determined gravimetrically.

The water absorption of a block copolymer built of polyamide blocks and of polyalkylene oxide blocks is determined in each case by producing a film of thickness 75 μm therefrom, weighing said film, storing same in water at 23° C. for 3 days and, after the surfaces of the film have been dried, determining the change of weight and stating this in percent [%].

The hydrophilic block copolymers suitable in the invention preferably have a higher, with preference at least 10% higher, preferably up to 30% higher, water absorption than corresponding, hydrophobic block copolymers. The water absorption of these, measured by the method mentioned before, is from 0% by weight to at most 2% by weight. A person skilled in the art can therefore use simple preliminary tests to determine whether the respective block copolymer is suitable for the inventive use.

The water absorption of a suitable hydrophilic block copolymer A) as film of thickness 75 μm is preferably at least 10% by weight, more preferably 20% by weight, still more preferably at least 24% by weight, most preferably up to 30% by weight, after storage for 72 h in water at 23° C., after the surfaces of the film have been dried, and using gravimetric determination of the change in weight.

The water vapor transmission rate of the hydrophilic block copolymer A) is preferably at least 1200 g/m$^2$·24 h, more preferably at least 1500 g/m$^2$·24 h, still more preferably at least 2000 g/m$^2$·24 h, and most preferably at least from 2500 to ≥3000 g/m$^2$·24 h (at 23° C., 100% relative humidity and film thickness: 75 μm) measured in accordance with ASTM F1249.

Hydrophilic block copolymers A) used in the invention are hydrophilic block copolymers made of at least one polyamide block and of at least one polyalkylene oxide block.

Polyalkylene oxide blocks used can be at least one polyalkylene oxide or alkylene oxide copolymer selected from the group comprising poly-$C_2$- to $C_4$-alkylene oxides, preferably polyethylene oxide, polypropylene oxide, polybutylene oxide, and copolymers of these, particularly preferably polyethylene oxide. The molar mass of a polyalkylene oxide block is preferably from 200 to 3000 g/mol.

According to one preferred embodiment the hydrophilic block copolymer A) comprises at least one polyalkylene oxide block made of $C_2$- to $C_4$-alkylene oxides, preferably made of ethylene oxide, propylene oxide, and/or butylene oxide.

According to another preferred embodiment the hydrophilic block copolymer A) comprises more than one polyalkylene oxide block, more preferably more than two, still more preferably ≥5, or up to 10, polyalkylene oxide blocks, where all of the polyalkylene oxide blocks are preferably composed of the same alkylene oxide.

The inventively used hydrophilic block copolymers A) have at least one polyamide block made of a polyamide homopolymer or polyamide copolymer. The polyamides (PA) and copolyamides (CoPA) are aliphatic, partial aromatic, or aromatic, and the molar mass of one polyamide block is preferably from 600 to 5000 g/mol. The melting point of the polyamide component is in the range from 160 to 240° C., more preferably from 170 to 220° C.

The polyamide block is preferably composed of a polyamide or copolyamide built of diamines such as aliphatic diamines having from 2 to 10 carbon atoms, in particular hexamethylenediamine, and/or aromatic diamines having from 6 to 10 carbon atoms, in particular p-phenylenediamine, and of dicarboxylic acids such as aliphatic or aromatic dicarboxylic acids having from 6 to 14 carbon atoms, in particular adipic acid, terephthalic acid (T), or isophthalic acid (I). Moreover, homo- or copolyamides can be produced from lactams having from 4 to 10 carbon atoms, e.g. from ε-caprolactam. Inventively used polyamides are preferably selected from the group comprising PA-6, PA-6,6, PA-6,9, PA-6,10, PA-6,12, PA-6,14, PA-6,18, PA-9,6, PA-11, PA-12, PA-6I, PA-6T, particular preference being given here to PA-6 and PA-12.

A detailed description of the composition of the PA and CoPA mentioned is moreover disclosed in Kunststoff-Handbuch volume VI, Polyamide [Polyamides], Carl Hanser Verlag Munich, 1966; and Melvin I. Kohan, *Nylon Plastics Handbook*, Carl Hanser Verlag, Munich, 1995, the entire content of which is incorporated herein in relation to the present disclosure.

In one preferred embodiment the hydrophilic block copolymer A) comprises at least one polyamide block built of an aliphatic polyamide selected from the group comprising PA-6, PA-6,6, PA-6,9, PA-6,10, PA-6,12, PA-6,14, PA-6,18, PA-9,6, PA-11 and PA-12, and having a molar mass of from 600 to 5000 g/mol per PA block.

According to one preferred embodiment the hydrophilic block copolymer A) has more than one polyamide block, more preferably more than two, still more preferably more than 5, up to 10, polyamide blocks, where the polyamide blocks are preferably composed of the same aliphatic homopolyamide or copolyamide.

Particularly preferably, the hydrophilic block copolymer A) comprises more than one polyamide block and more than one polyalkylene oxide block, and the polyamide blocks are preferably composed of the same homopolyamide or copolyamide as well as the polyalkylene oxide blocks are composed of the same alkylene oxide.

According to one preferred embodiment the polyamide content of the hydrophilic block copolymer A) is at least 50% by weight, preferably from 50 to 90% by weight, based on the total weight of the hydrophilic block copolymer A).

The production of the hydrophilic block copolymer A) is known, and can preferably be carried out by copolycondensation of at least one polyamide block having terminal reactive groups with at least one polyalkylene oxide block having terminal reactive groups, where ester groups or amide groups are built as linkages.

For the regulation of the water vapor transmission rate of the inventive breathable film, the film has at least one thermoplastic polymer B) which regulates the water vapor transmission rate.

It is preferable that the hydrophilicity of the thermoplastic polymer B) regulating the water vapor transmission rate of the polymer component A) is lower than that of the hydrophilic block copolymer A), preferably by at least 10%, still more preferably by at least 20%, very particularly preferably by 30%, said hydrophilicity being determined gravimetrically as described before by the water absorption of a film of thickness 75 μm after storage in water at 23° C. for 72 h. The water absorption of the polymer B should be from 0% by weight to at most 2% by weight, preferably to at most 1.5% by weight, still more preferably from 0% by weight to <1% by weight. Polymers suitable as thermoplastic polymers B) for regulating the water vapor transmission rate are at least one polymer selected from the group comprising polyolefins, preferably polyethylenes such as LDPE, LLDPE, m-PE, HDPE, or polypropylenes, very particularly preferably LDPE, olefin copolymers, preferably propylene/ethylene copolymers, polyvinyl alcohols, ethylene/vinyl alcohol copolymers, olefin/vinyl ester copolymers, preferably ethylene/vinyl ester copolymers, particularly preferably ethylene/vinyl acetate copolymers, lactic acid homo- and copolymers, preferably polylactides, polyhydroxyalkanoates, (alkyl) (meth)acrylate homo- and copolymers, preferably ethylene/butyl acrylate copolymers, ethylene/methyl acrylate copolymers, cycloolefin copolymers, preferably ethylene/norbornene copolymers, thermoplastic starch, polystyrenes, styrene (block) copolymers, preferably styrene/butadiene block copolymers, styrene/isoprene block copolymers, styrene/acrylate nitrile copolymers, acrylonitrile/butadiene/styrene copolymers, block copolymers made of at least one polyamide block and one polyalkylene oxide block with a water absorption, determined by the method mentioned before, that is at least <2% by weight, preferably from 0% by weight to <1% by weight, and mixtures of at least two of the polymers mentioned, in an amount of at least 10% by weight, based on the total weight of the mixture of the polymer components A) and B).

A material preferably suitable as a polymer B) for regulating the water vapor transmission rate is at least one thermoplastic olefin homo- or copolymer, particularly preferably a polyethylene, in particular LDPE, or an ethylene copolymer, particularly preferably an ethylene/vinyl acetate copolymer.

In one preferred embodiment the amount of the hydrophilic block copolymer A) in the mixture is at least 30% by weight, more preferably from 40 to 90% by weight, particularly preferably from 40 to 65% by weight, or preferably from 65 to 90% by weight, particularly preferably from 75 to 85% by weight, based on the total weight of the mixture of the polymer components A) and B), depending on the respective application sector and thus on the required water vapor transmission rate of the product.

The inventive breathable film is preferably based on a mixture comprising at least 10% by weight, more preferably at least 15% by weight, particularly preferably at least 20% by weight, of the thermoplastic polymer B) regulating the water vapor transmission rate, based on the total weight of the mixture of the polymer components A) and B).

The proportion of the polymer B) is preferably in the range of at most 70% by weight, more preferably from 10 to 60% by weight, particularly preferably from 35 to 60% by weight, or preferably from 10 to 35% by weight, particularly preferably from 15 to 25% by weight, based on the total weight of the mixture of the polymer components A) and B).

The desired water vapor transmission rate of an inventive breathable film can be established via an appropriate selection of the mixing ratio of the hydrophilic block copolymer A) to the polymers B) defined in the invention.

To the extent that the inventive film is multilayered, it is also possible to produce a breathable film with a graduated water vapor transmission rate by providing a film comprising layers having a different water vapor transmission rate. Thus, it is possible to establish an appropriately oriented water vapor transmission rate according to the required functionality.

According to one preferred embodiment the inventive single-layer, breathable film is based on a polymer mixture composed of from 40 to 90% by weight of at least one hydrophilic, elastomeric block copolymer A), and of from 10 to 60% by weight of at least one of the thermoplastic polymers B) mentioned, and also optionally of conventional auxiliaries C), whereby the entirety of components A) to C) must always add up to 100% by weight.

According to another preferred embodiment, the inventive breathable film is based on a mixture of from 40 to 65% by weight of at least one hydrophilic, elastomeric block copolymer A), of from 35 to 60% by weight of at least one of the thermoplastic polymers B) mentioned, and optionally of conventional auxiliaries C), whereby the entirety of components A) to C) must always add upt to 100% by weight.

According to another preferred embodiment, the inventive breathable film is based on a mixture of from 65 to 90% by weight of at least one hydrophilic, elastomeric block copolymer A), and of from 10 to 35% by weight of at least one thermoplastic polymer B), and optionally of conventional auxiliaries C), whereby the entirety of components A) to C) must always add up to 100% by weight.

Optionally, the breathable film of the invention can comprise one or more conventional auxiliaries C), such as UV stabilizers, antiblocking agents, pigments, antistatic agents, antimicrobial substances, primers to improve adhesive anchoring, processing aids, lubricants, antifogging additives, and/or dyes, in the usual quantities.

The inventive breathable film can be produced by known, preferably continuous processes, e.g. by extrusion, preferably by blown-film extrusion, in the form of a film bubble, or by a cast-extrusion process as flat film. These processes are known to the person skilled in the art.

In one preferred embodiment, the inventive film is produced in the form of an extruded film bubble. The blow-up ratio of the extruded film can preferably be at least 1:1, particularly preferably at least 1.5:1, and very particularly preferably at least 2:1.

The preferably extruded film bubble can be processed to give a collapsed, optionally full-width, flat film.

The inventive film can also be produced by a cast-extrusion process.

The inventive film can optionally be stretched at least monoaxially with a stretching ratio of at least 1:1.5, particularly preferably of at least 1:2, particularly preferably from 1:2 to 1:4, or biaxially, preferably in the ratio of longitudinal to transverse stretching of at least 1:1, particularly preferably at least 1.1:1, and very particularly preferably at least 1.2:1.

In order to avoid shrinkage, the inventive stretched film can be fixed by using an appropriate temperature treatment after stretching.

The inventive breathable film can comprise one or more layers. The inventive breathable film preferably has one layer.

Insofar as the film has two or three layers, the individual layers can have the same, or a different, composition of the polymer components A) and B), and thus can have different water vapor transmission rates, so that it is possible to obtain an asymmetric multilayer film with an appropriately oriented water vapor transmission rate corresponding to the intended application.

In one preferred embodiment the inventive breathable film has at least two layers, preferably at least three layers, having mixing ratio of the hydrophilic block copolymer A) to the polymer B) in the individual layers selected in such a way that the individual layers have different water vapor transmission rates. It is preferable that the water vapor transmission rate increases or decreases from one surface layer to the other surface layer of the breathable film; by way of example, therefore, an internal layer can be adjacent to a layer with higher water vapor transmission rate as well as to a layer with lower water vapor transmission rate.

This type of breathable film with graduated water vapor transmission rate is particularly advantageous for the production of building sheeting, in particular roof-lining membranes or roof linings, in order to achieve efficient dissipation of water vapor from a building, but preventing ingress of water vapor from the atmosphere into the interior of said building.

Inventive, multilayer films can also be produced by coextrusion, as described above.

The thickness of the inventive breathable film is preferably in the range from 20 to 300 µm, more preferably from 30 to 200 µm; the thickness of the film can vary in accordance with the field of application.

The water vapor transmission rate of the breathable film of the invention is not based on any mechanical operation carried out on the film, for example perforation or other measures leading to micropores, but instead caused solely by the use of the inventive mixture comprising the polymer components A) and B) for the production of the inventive film. The inventive film therefore does not have any porosity of any type like in form of micropores, for example. The water vapor transmission rate of the inventive breathable film depending on the intented use is from 20 to ≥3000 g/m$^2$·24 h (at 23° C. and 100% relative humidity, film thickness: 75 µm) measured in accordance with ASTM F1249.

According to one preferred embodiment the water vapor transmission rate of the breathable, preferably single-layer, inventive film is from 20 to 2000 g/m$^2$·24 h, preferably from 80 to 1500 g/m$^2$·24 h, particularly preferably from 100 to 1000 g/m$^2$·24 h (at 23° C. and 100% relative humidity, film thickness: 75 µm) measured in accordance with ASTM F1249.

Inventive, breathable films with these water vapor transmission rate values are particularly suitable for the production of roof-lining membranes or roof linings, or for the production of adhesive tapes, preferably of adhesive tapes used in the construction sector.

The present invention therefore also provides the use of an inventive breathable film with such water vapor transmission rate as substrate layer of an adhesive tape, preferably of an adhesive tape used in the construction sector.

These inventive adhesive tapes are composed of the inventive breathable film as substrate layer, of an adhesive layer, optionally of a lattice scrim arranged therebetween, preferably made of viscose fibers, polyester fibers, or polypropylene fibers, and optionally of a releasable protective film arranged on top of the adhesive layer.

According to the invention, it is preferable that such adhesive layer is based on acrylate-based adhesives. These acrylate adhesives can preferably be applied either as dispersion or as hot-melt adhesives intended for crosslinking by UV radiation, to the substrate layer. Other types of application are equally possible.

The adhesive layer can moreover also be based on other pressure-sensitive adhesive types, e.g. adhesives based on synthetic rubber, for example styrene-isoprene-styrene copolymers or styrene-butadiene copolymers, or adhesives based on polysilicone or on polyurethane.

According to one preferred embodiment the adhesive layer is based on at least one adhesive selected from the group comprising adhesives based on polyacrylates or on acrylate copolymers, adhesives based on synthetic rubber, preferably based on styrene-isoprene-styrene copolymers or on styrene-butadiene copolymers, adhesives based on polysilicones, adhesives based on polyurethanes, and mixtures of at least two of the adhesives mentioned.

In order to restrict elongation and improve stability, there can be a braid lattice scrim incorporated between the substrate layer and the adhesive layer or within the adhesive layer. The lattice scrim can be composed of an optionally woven, fibrous material. The lattice scrim is preferably composed of viscose fibers, polyester fibers such as PET fibers, polypropylene fibers, or a mixture thereof.

The water vapor transmission rate of the inventive film as substrate layer for an adhesive tape is particularly preferably at least 20 g/m$^2$·24 h, with preference from to 300 g/m$^2$·24 h, more preferably from 50 to 200 g/m$^2$·24 h measured in accordance with ASTM F1249 (at 23° C., 100% relative humidity, film thickness: 75 µm).

The water vapor transmission rate of an inventive adhesive tape with total thickness from 50 to 500 µm is particularly preferably at least 20 g/m$^2$·24 h, measured in accordance with ASTM F1249 (at 23° C., 100% relative humidity).

The water-vapor-diffusion-equivalent air-layer thickness $s_d$ of the inventive adhesive tapes composed of the inventive breathable film as substrate layer, of an adhesive layer, and of the lattice scrim is preferably at most 12 m, more preferably at most 10 m, still more preferably at most 8 m, and most preferably at most 5 m, measured in accordance with DIN 52615.

An example of a releasable protective film that can be used, arranged on top of the adhesive layer, is a single- or double-sided siliconized paper or a plastics film. The external side of the substrate film can also have a polysilicone coating which serves as protective film, so that the inventive adhesive tape can be wound up against itself without any protective film.

According to the invention, it is also possible that the substrate layer of the inventive adhesive tape comprises a plurality of layers, preferably at least two layers, where the layers can have the same or a different composition and thus can have different water vapor transmission rates. It is thus possible to achieve not only an appropriately oriented water vapor transmission rate of the adhesive tape but also an improved anchoring of the adhesive layer.

According to another embodiment the substrate film of the inventive adhesive tape has at least two layers; the layers here can have a different composition and thus different water vapor transmission rates.

The present invention further provides the use of the inventive breathable film as large-surface-area sheeting material, preferably in the construction sector, particularly preferably as roof-lining membrane or as part of roof linings.

According to the invention, the expression "roof-lining membrane" means a large-surface-area sheeting material arranged below the actual covering or external layer on a roof of a building, and above the insulating layer.

According to the invention, the expression "roof lining" means an envelope arranged below the actual roof covering or external layer, and above the insulating layer, and made of roof-lining membrane preferably adhesive-bonded by inventive adhesive tapes, in a roof of a building.

The invention further provides an inventive roof-lining membrane comprising at least one inventive breathable film and optionally at least one nonwoven layer, preferably a nonwoven layer made of polyethylene fibers, polyester fibers, or polypropylene fibers.

The inventive breathable film can be laminated or extruded onto the nonwoven layer; the inventive film can have a nonwoven layer only on one side or on both sides.

The nonwoven layer can be a synthetic or natural nonwoven material. It is particularly preferable that the nonwoven material is based on polyethylene fibers, polyester fibers, or polypropylene fibers, or on other thermoplastic fibers.

It is preferable that the water vapor transmission rate of the inventive breathable film as roof-lining membrane or as part of a roof lining is at least from 20 to 1000 g/m²·24 h, with preference from 30 to 500 g/m²·24 h, particularly preferably from 50 to 200 g/m²·24 h, measured in accordance with ASTM F1249 (at 23° C., 100% relative humidity, film thickness: 75 µm).

The water-vapor-diffusion-equivalent air-layer thickness $s_d$ of the inventive roof-lining membrane is preferably at most 10 m, more preferably at most 6 m, still more preferably at most 3 m, and most preferably at most 1 m, measured in accordance with DIN 52615.

According to another embodiment the roof-lining membrane comprises an inventive multilayer breathable film of which the individual layers can have different water vapor transmission rate and are arranged in such a way that the entire roof-lining membrane has an appropriately oriented water vapor transmission rate.

The invention further provides an inventive roof lining, composed of an inventive roof-lining membrane, preferably bonded by inventive adhesive tapes.

According to the invention these roof linings can preferably also have an appropriately oriented water vapor transmission rate resulting from an asymmetric, multilayer structure of the inventive roof-lining membrane, and also of the inventive adhesive tape.

According to another preferred embodiment the water vapor transmission rate of the inventive breathable film is at least 500 g/m²·24 h, preferably at least 1000 g/m²·24 h, and particularly preferably at least from 1500 to ≥3000 g/m²·24 h measured in accordance with ASTM F1249 (at 23° C. and 100% relative humidity, film thickness: 75 µm).

Breathable films of this type are particularly suitable as protective films, preferably underwear-protecting films, for hygiene products, in particular for sanitary towels, or incontinence products, or as substrate layer for plasters.

In the case of plasters, which are used inter alia for the protection of wounds, the inventive breathable films are also suitable as substrate layers which face away from the skin. These substrate layers should preferably be breathable, i.e. permeable to water vapor, in order that if the plaster remains in place for a prolonged period there is sufficient dissipation of water vapor that is emitted via excretions such as sweat from the region of skin covered by the plaster. This applies equally to protective films, in particular underwear-protecting films, present on the side facing away from the body in a hygiene product or incontinence product, for the protection of underwear. These protective films must equally be breathable, in order that water vapor emitted from the body via sweating is transported sufficiently rapidly into the exterior environment.

The water vapor transmission rate of these breathable protective films is preferably at least 500 g/m²·24 h, with preference at least 1000 g/m²·24 h, with very particular preference from 1500 g/m²·24 h to 2500 g/m²·24 h, in particular up to ≥3000 g/m²·24 h (at 23° C. and 100% relative humidity, film thickness: 75 µm).

The present invention therefore further provides the use of an inventive breathable film with such mentioned water vapor transmission rate values as substrate layer for plasters, in particular wound plasters, or as water-impermeable, but breathable protective film of hygiene products, in particular of sanitary napkins, or of incontinence products.

The present invention therefore also provides a plaster with an external substrate layer made of an inventive breathable film with a water vapor transmission rate stated above.

The present invention therefore also provides hygiene products, in particular sanitary napkins, or incontinence products with an inventive breathable film as protective film facing away from the body side, preferably underwear-protecting film, which protective film has the water vapor transmission rate mentioned before for such application sector.

EXAMPLE 1

FIG. 1 shows the dependency of the water vapor transmission rate of a mixture of polyethylene (LDPE) and a hydrophilic block copolymer made of PA-6 blocks and of polyethylene oxide blocks with water absorption of 28% by weight, determined by the method disclosed before, with different mixing ratios of A and B.

The water vapor transmission rate was measured of the film produced of the before mentioned polymer mixture by blown-film extrusion as a single-layer film with a thickness of 75 µm. The water vapor transmission rate thereof was determined in accordance with ASTM F1249 at 23° C. and 100% relative humidity in a Permatran-W-Twin with the aid of an infrared sensor, by determining the quantity of water vapor diffusing through the respective sample of the resultant film.

It was found that by increasing the quantity of the LDPE in the mixture stepwise a significant reduction of water vapor transmission rate from >2000 g/m²·24 h began already when as little as 10% by weight of LDPE was added, and a value below 100 g/m²·24 h was achieved when the ratio by weight of the block copolymer to LDPE was 50:50.

EXAMPLE 2

Figure 2:
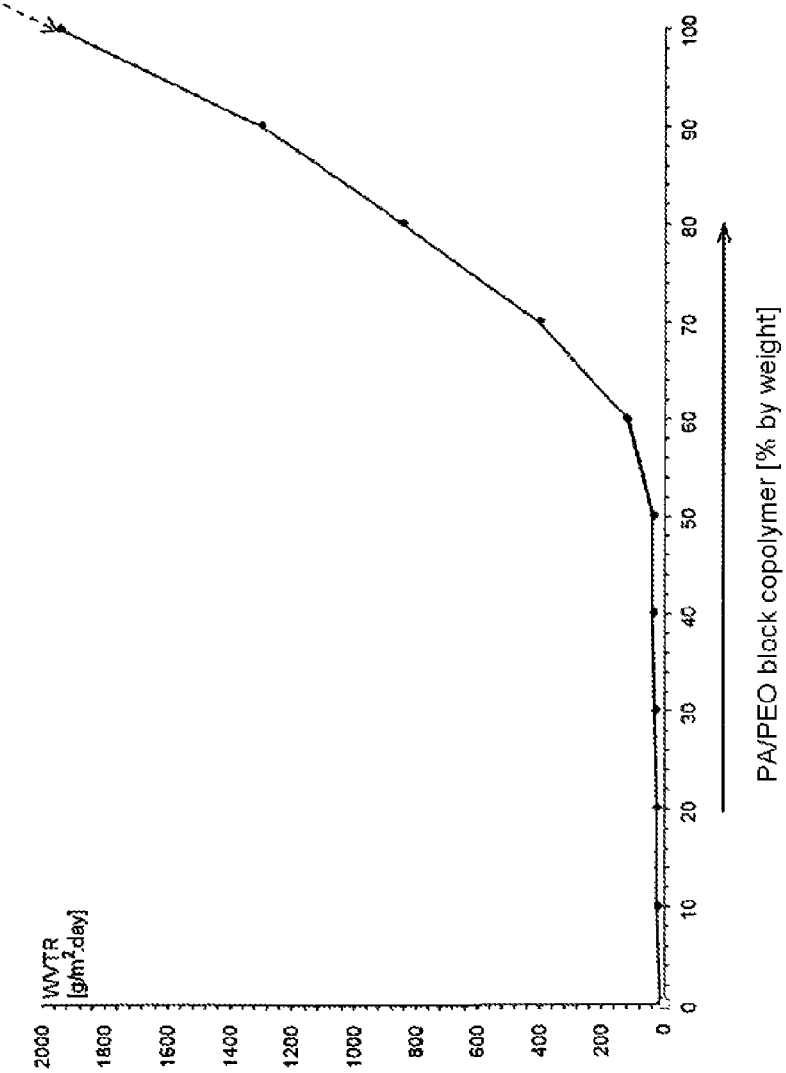
FIG. 2 is a graph of water transmission rates of films obtained of mixtures containing different quantities of ethylene/vinyl acetate copolymers.

As shown in FIG. 2, in the case of films obtained of mixtures containing different quantities of ethylene/vinyl acetate copolymers, having a proportion of 17.5% by weight of vinyl acetate, to the block copolymers described in example 1 and made of PA-6 and of polyethylene oxide blocks, the initial water vapor transmission rate of >2000 g/m²·24 h, measured in accordance with ASTM F1249 at 23° C. and 100% relative humidity, is reduced by increasing the quantity of the ethylene/vinyl acetate copolymer in such mixtures used for producing films. Films with a thickness 75 µm were produced by blown-film extrusion from the respective mixtures with different % by weight of ethylene/vinyl acetate copolymer, and the water vapor transmission rate of such films was measured by the method described before, and presented in FIG. 2. At a ratio by weight of 60% by weight of block copolymer to 40% by weight of ethylene/vinyl acetate copolymer the water vapor transmission rate has already decreased to ≤100 g/m²·24 h.

From the two figures it can be derived that an inventive breathable film with a required water vapor transmission rate for a special use can be found and formulated accordingly by simple preliminary experiments.

What is claimed is:

1. A single-layer or multilayer, breathable film which repels aqueous liquids, and of which the water vapor transmission rate is from 20 to 3000 g/m² 24 h (at 23° C., 100% relative humidity and film thickness: 75 µm) measured in accordance with ASTM F1249, comprising at least one layer based on a polymer mixture of A) from 40 to 90% by weight of at least one hydrophilic, elastomeric block copolymer with a water vapor transmission rate of at least 1200 g/m² 24 h, determined as mentioned before, built of at least one polyamide block and of at least one polyalkylene oxide block having a molar mass from 200 to 3000 g/mol, B) for regulating the water vapor transmission rate of the breathable film from 10 to 60% by weight of at least one thermoplastic ethylene/vinyl ester copolymer, wherein the gravimetrically measured water absorption of the ethylene vinyl ester copolymer is ≤2% by weight, and C) optionally conventional auxiliaries, selected from the group consisting of UV stabilizers, antiblocking agents, pigments, antistatic agents, antimicrobial substances, primers to improve adhesive anchoring, processing aids, lubricants, antifogging additives, and dyes, whereby all the components A) to C) must add up always to 100% by weight.

2. The breathable film as claimed in claim 1, wherein the gravimetrically measured water absorption of the hydrophilic block copolymer A) with film of thickness of 75 μm at 23° C. after 72 h in water at 23° C. is at least 10% by weight.

3. The breathable film as claimed in claim 1, wherein the polyamide content of the hydrophilic block copolymer A) is at least 50% by weight, based on the total weight of the hydrophilic block copolymer A).

4. The breathable film as claimed in claim 1, wherein the hydrophilic block copolymer A) is composed of at least one polyamide block made of an at least aliphatic, partial aromatic, or aromatic polyamide.

5. The breathable film as claimed in claim 3, wherein the hydrophilic block copolymer A) has a plurality of polyamide blocks, of which all of the polyamide blocks are composed of the same polyamide or copolyamide.

6. The breathable film as claimed in claim 1, wherein the hydrophilic block copolymer A) has at least one polyalkylene oxide block made of $C_2$- to $C_4$-alkylene oxides.

7. The breathable film as claimed in claim 6, wherein the hydrophilic block copolymer A) comprises a plurality of polyalkylene oxide blocks.

8. The breathable film as claimed in claim 1, wherein the film has at least two layers, of which each layer has a different water vapor transmission rate.

9. The breathable film as claimed in claim 1, wherein the water vapor transmission rate of the film is from 20 to 2000 $g/m^2$ 24 h (at 23° C. and 100% relative humidity and a film thickness: 75 μm).

10. A substrate film of an adhesive tape applicable in the construction sector comprising the breathable film of claim 1.

11. An adhesive tape composed of a breathable film as claimed in claim 9 as substrate layer, of an adhesive layer, of optionally a lattice scrim arranged there between, and of optionally a releasable protective film on top of the adhesive layer.

12. The adhesive tape as claimed in claim 11, wherein the adhesive layer is based on at least one adhesive selected from the group consisting of adhesives based on polyacrylates or on acrylate copolymers, adhesives based on synthetic rubber, adhesives based on polysilicones, and adhesives based on polyurethanes.

13. The adhesive tape as claimed in claim 11, wherein the total thickness of the adhesive tape is from 50 to 500 μm and its water vapor transmission rate is at least 20 $g/m^2$ 24 h.

14. A large-surface-area sheeting material in the construction sector, comprising the breathable film of claim 1.

15. A roof-lining membrane comprising at least one breathable film as claimed in claim 1 and optionally at least one nonwoven layer.

16. A roof lining composed of a roof-lining membrane bonded by the adhesive tape as claimed in claim 11.

17. A protective film of a hygiene product, comprising the breathable film of claim 1.

18. A protective film of a hygiene product such as a sanitary napkin, or of an incontinence product, comprising a breathable film as claimed in claim 1, with water vapor transmission rate at least 1000 $g/m^2$ 24 h, up to 2500 $g/m^2 \cdot 24$ h (at 23° C. and 100% relative humidity, film thickness: 75 μm), measured in accordance with ASTM F1249.

* * * * *